(12) United States Patent
Nash et al.

(10) Patent No.: US 6,286,509 B1
(45) Date of Patent: Sep. 11, 2001

(54) INTRODUCERS AND TUBE ASSEMBLIES

(75) Inventors: John Edward Nash, Hythe; Simon Neame, Broadstairs; Eric Pagan, Hythe, all of (GB)

(73) Assignee: Smiths Group PLC, London (GB)

( * ) Notice: Subject to any disclaimer, the term of this patent is extended or adjusted under 35 U.S.C. 154(b) by 0 days.

(21) Appl. No.: 09/386,226

(22) Filed: Aug. 31, 1999

(30) Foreign Application Priority Data

Sep. 5, 1998 (GB) .................................................. 9819330

(51) Int. Cl.$^7$ .................................................. A61M 16/00
(52) U.S. Cl. .................................. 128/207.14; 128/200.26
(58) Field of Search ..................... 128/207.14, 207.15, 128/200.26, 911, 912, DIG. 26, 207.18; 606/108; 604/265, 164.01, 164.13, 165.01; 600/185, 194

(56) References Cited

U.S. PATENT DOCUMENTS

| | | | | |
|---|---|---|---|---|
| 4,246,897 | * | 1/1981 | Muto | 128/207.14 |
| 4,637,388 | * | 1/1987 | Melendy | 128/207.14 |
| 4,655,214 | * | 4/1987 | Linder | 128/207.14 |
| 5,222,487 | * | 6/1993 | Carr et al. | 128/200.26 |
| 5,279,610 | * | 1/1994 | Park et al. | 128/200.26 |
| 5,546,937 | * | 8/1996 | Stuart et al. | 128/207.15 |
| 5,749,357 | * | 5/1998 | Linder | 128/207.14 |
| 5,791,338 | * | 8/1998 | Merchant et al. | 128/200.26 |
| 5,919,183 | * | 7/1999 | Field | 128/207.14 |
| 5,928,198 | * | 4/1999 | Lester | 128/207.14 |
| 6,053,166 | * | 4/2000 | Gomez | 128/207.26 |

FOREIGN PATENT DOCUMENTS

WO 94/11048   5/1994  (WO).
WO 98/52637  11/1998  (WO).

* cited by examiner

Primary Examiner—John G. Weiss
Assistant Examiner—Teena Mitchell
(74) Attorney, Agent, or Firm—Connolly Bove Lodge & Hutz, LLP

(57) ABSTRACT

A tracheostomy tube obturator has a patient end nose protruding from the patient end of the tube. A passage for a guide wire extends through the nose of the obturator at an angle to its axis. The aperture through which the passage opens at the patient end of the obturator lies on a plane extending at right angles to the passage and inclined away from the normal to the axis of the nose by about 8°.

7 Claims, 3 Drawing Sheets

Fig.1. PRIOR ART
PRIOR ART
Fig.2.
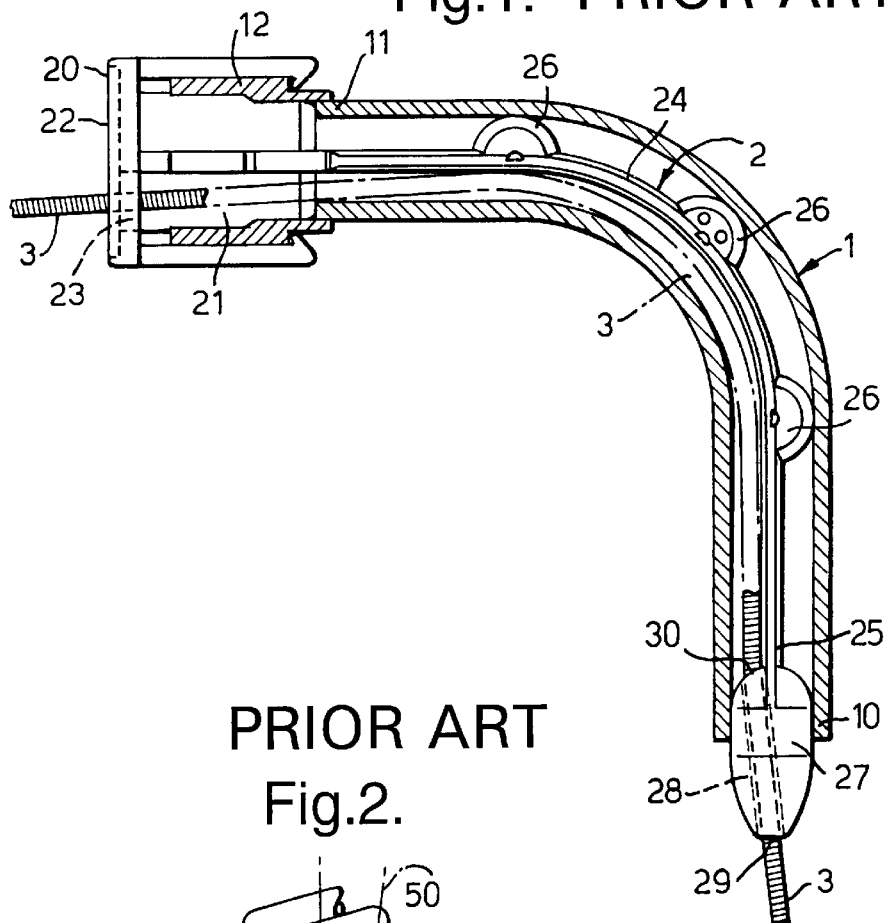
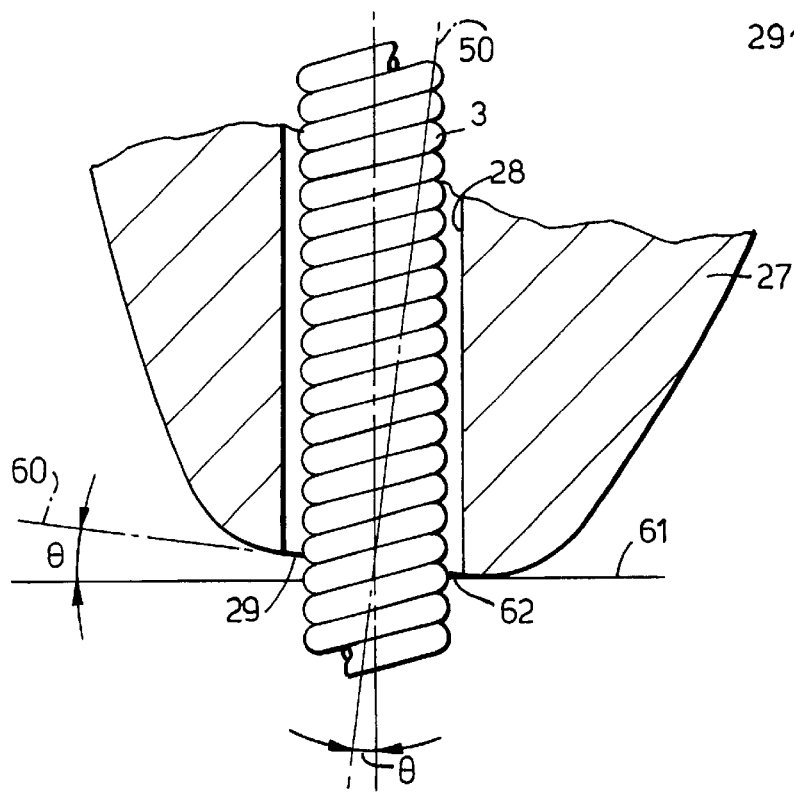

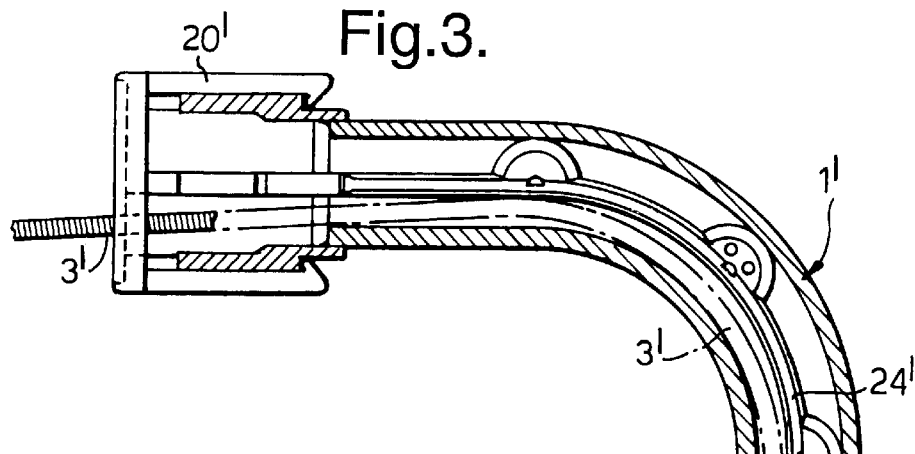
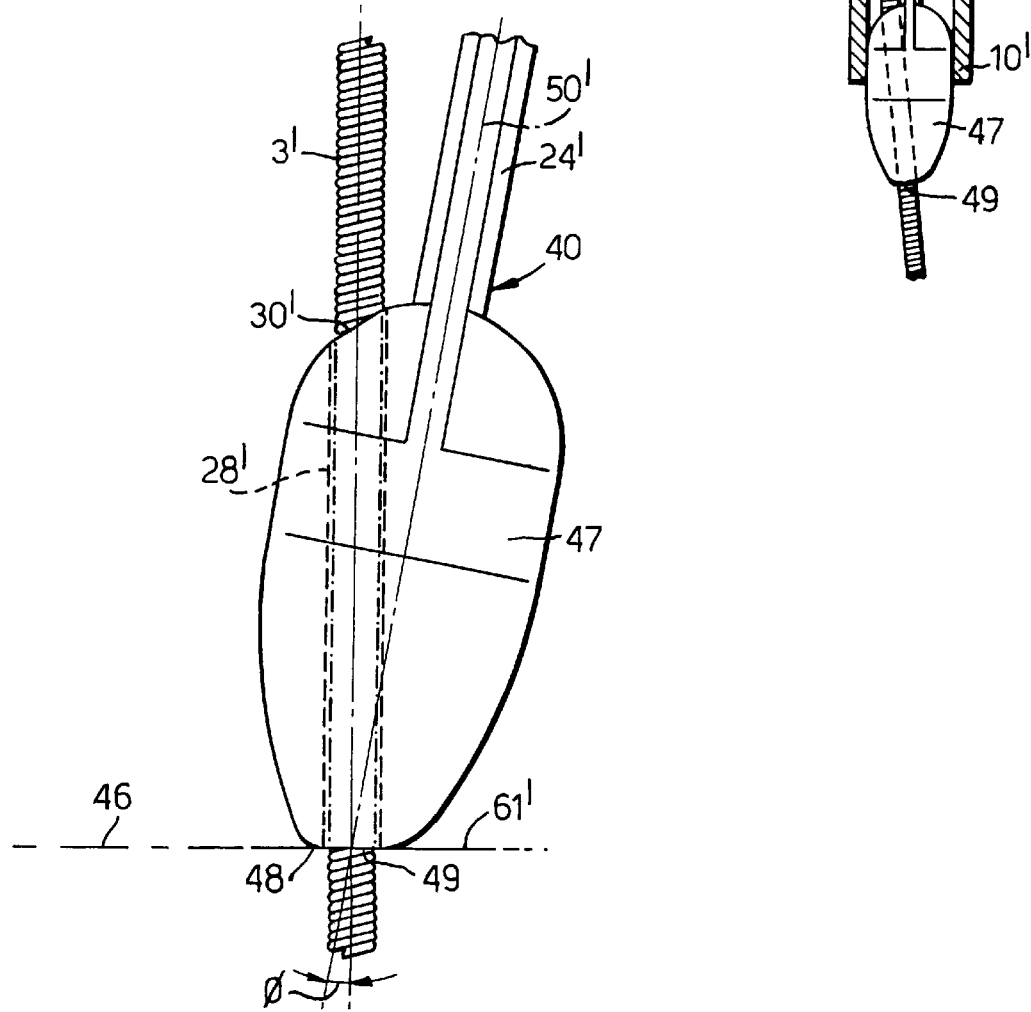

INTRODUCERS AND TUBE ASSEMBLIES

BACKGROUND OF THE INVENTION

This invention relates to introducers and to tube assemblies including an introducer.

Where a tube is to be introduced through an opening formed in the skin or other tissue, this may be done by first inserting a guide wire through the opening. An assembly of the tube with an introducer, such as an obturator inserted within it, is then slid along the guide wire. The guide wire and obturator are subsequently removed, leaving the tube in position. Examples of obturators are described, for example, in GB2316321, U.S. Pat. Nos. 4,246,897, 5,222,487 and GB2224213. The obturator typically has a nose with a pointed end protruding from the patient end of the tube. The nose is provided at the patient end of a strap, the machine end of which has a mount fitted with the machine end of the tube. The nose has a passage through which the guide wire extends, the passage opening through an aperture located centrally at the patient end and, at its opposite end, through an aperture displaced to one side of the strap, so that the passage is inclined away from the axis of the nose. The plane in which the patient end aperture lies extends at right angles to the axis of the nose and, therefore, at an angle to the guide wire passage. This arrangement means that, when the tube assembly is slid along the guide wire, the patient end surface of the obturator will meet the tissue surface at an angle. As a result of this, a potential tissue pinch point is created between the guide wire and one side of the obturator nose.

BRIEF SUMMARY OF THE INVENTION

It is an object of the present invention to provide an alternative introducer and tube assembly including an introducer.

According to one aspect of the present invention there is provided an introducer for a medical tube, the introducer having a patient end nose a part of which is arranged to protrude from a patient end of the tube, and the nose having a passage therethrough for receiving a guide wire, the passage opening at the patient end of the nose through an aperture that lies on a plane extending at right angles to the passage and inclined away from the normal to the axis of the nose.

The aperture preferably lies on a plane inclined away from the normal to the axis of the nose at an angle of about 8°. The introducer may include a mount at its machine end adapted to engage the machine end of the tube, and a strap extending between the nose and the mount.

According to another aspect of the present invention there is provided an assembly including a medical tube and an introducer according to the above one aspect of the invention.

The medical tube is preferably a tracheostomy tube and the assembly may include a guide wire.

A tracheostomy tube assembly including an obturator and guide wire, according to the present invention, will now be described, by way of example, with reference to the accompanying drawings.

BRIEF DESCRIPTION OF THE DRAWINGS

FIG. 1 is a sectional side elevation view of a conventional, prior art assembly;

FIG. 2 is an enlarged sectional side elevation view of a part of the patient end of the obturator of the assembly of FIG. 1;

FIG. 3 is a sectional side elevation view of the assembly of the present invention;

FIG. 4 is an enlarged side elevation view of the patient end of the obturator of the assembly of FIG. 3;

DETAILED DESCRIPTION OF THE PREFERRED EMBODIMENT

Figure 5:
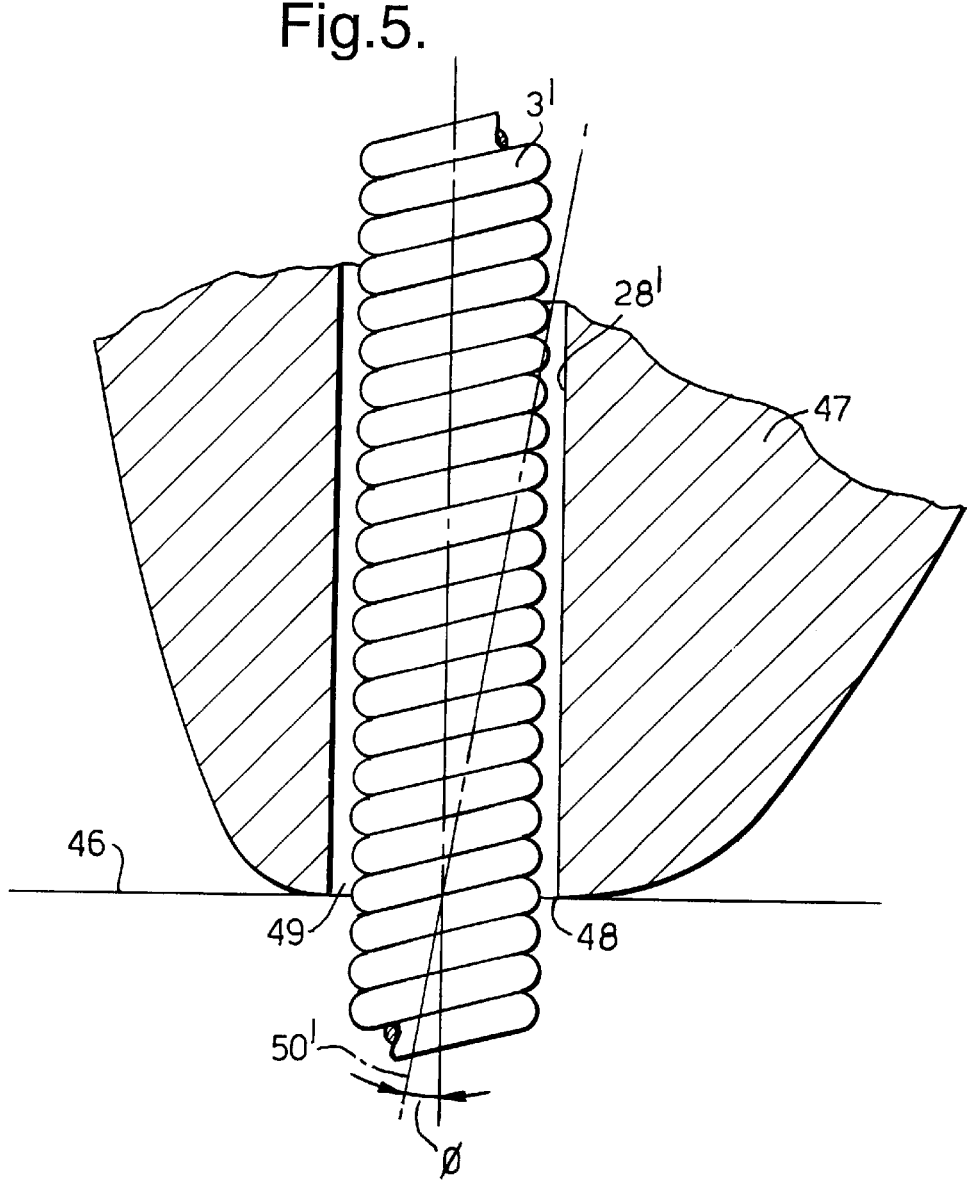
FIG. 5 is a further enlarged sectional side elevation view of a part of the patient end of the obturator shown in FIG. 4.

With reference first to FIGS. 1 and 2, the conventional assembly includes a tracheostomy tube 1, an introducer in the form of an obturator 2, and a guide wire 3.

The tracheostomy tube 1 is entirely conventional, with a curved shape and having a patient end 10 and a machine end 11 provided with a coupling 12.

The obturator 2 is of a stiff but bendable plastics material with a mount 20 at its machine end shaped to engage the inside and outside of the coupling 12, to retain the obturator in the tube 1. The mount 20 has a part 21 of cruciform section making a friction fit within the coupling 12. A flange 22 at the rear end of the mount 20 has apertures 23 through which the guide wire 3 extends. A strap 24 extends from the mount 20 to the patient end 25 of the obturator 2. The strap 24 is of generally rectangular shape along most of its length, the width of the strap in a plane at right angles to the plane of curvature of the tube 1 being just less than the inside diameter of the tube. The thickness of the strap 24, in the plane of curvature of the tube 1, is less than its width so that it is relatively flexible in this plane but is relatively inflexible in the plane at right angles to the plane of curvature and has sufficient axial rigidity to enable it to be slid into the tube. The strap 24 also has three semicircular projections 26 on the outside of its curvature, shaped to contact the inside of the tube 1. At its patient end 25, the obturator 2 has a nose 27 of bullet or olive shape arranged to protrude from the patient end 10 of the tube 1. A guide wire passage 28 extends through the nose 27 from an aperture 29 located centrally at its patient end to an aperture 30 displaced to one side of the axis of the nose. The passage 28 extends as a straight line so as to facilitate manufacture and to enable the guide wire 3 to slide freely within the passage. The passage 28 is inclined at an angle θ of about 8° away from the axis 50 of the nose 27 and the patient end of the tube 1. The aperture 29 lies on a plane 60, therefore, inclined at an angle θ of about 8° to the surface 61 of skin through which the guide wire 3 extends. This creates a potential tissue pinch point 62 between the guide wire 3 and the leading edge of the aperture 29 because the initial contact of the obturator 2 with the skin surface 61 is displaced to one side of the guide wire.

Figure 6:
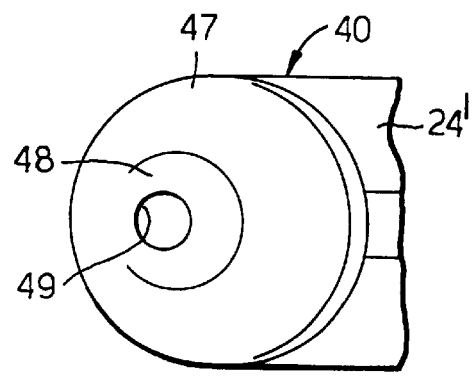
FIG. 6 is an end view of the patient end of the obturator.

With reference now to FIGS. 3 to 6, the assembly of the present invention is identical with that described with reference to FIGS. 1 and 2 except in respect of the nose 47 of the obturator 40. Features identical with those in the conventional assembly are given the same reference numerals with the addition of a prime'. The obturator 40 is a single-piece moulding of high-density polyethylene. The nose 47 shown in FIGS. 3 to 6 is similar to the nose 27 except that the normal to the plane 46 of its tip end surface 48, including the aperture 49 opening from the guide wire passage 28', is inclined at an angle φ of about 8° away from the axis 50' of the nose and the patient end of the tube 1'. Thus, the tip end surface 48 is inclined at right angles to the axis of the guide wire passage 28', which extends in a straight line from the patient end aperture 49 to the machine end aperture 30'. The patient end of the nose 47 thereby has an asymmetric appearance about its axis.

With this arrangement, when the obturator 40 is slid along the guide wire 3' projecting from the skin or other tissue surface 61', the tip 48 of the obturator will contact the tissue surface squarely, without any pinch points.

It will be appreciated that the asymmetric tip could be used on other introducers or obturators and is not confined to use with tracheostomy tubes.

What we claim is:

1. An introducer for a medical tube having a patient end and a machine end, the introducer comprising: a machine end; a patient end nose having an axis and a patient end being arranged to protrude from a patient end of a tube; a passage extending through said patient end nose for receiving a guide wire; and an aperture through which said passage opens at a patient end of said patient end nose, the plane of said aperture extending at right angles to said passage and inclined away from a line at right angles to said axis.

2. An introducer according to claim 1, wherein the plane of said aperture is inclined away from the said line at right angles to said axis at an angle of about 8°.

3. An introducer according to claim 2, wherein said introducer includes a mount at its machine end adapted to engage a machine end of said tube, and a strap extending between said nose and said mount.

4. An introducer according to claim 1, wherein said introducer includes a mount at a machine end adapted to engage a machine end of said medical tube, and a strap extending between the said patient end nose and said mount.

5. An assembly including in combination a medical tube having a patient end and a machine end and an introducer, said introducer comprising: a patient end nose having a patient end arranged to protrude from a patient end of said tube; a passage extending through said patient end nose for receiving a guide wire; and an aperture through which said passage opens at a patient end of said patient end nose, the plane of said aperture extending at right angles to said passage and inclined away from a line at right angles to said axis.

6. An assembly including a tracheostomy tube having a patient end and a machine end and an introducer, said introducer comprising: a patient end nose having a patient end arranged to protrude from the patient end of said tracheostomy tube; a passage extending through said patient end nose for receiving a guide wire; and an aperture through which said passage opens at the patient end of said patient end nose, the plane of said aperture extending at right angles to said passage and inclined away from a line at right angles to said axis.

7. An assembly including a tracheostomy tube having a patient end and a machine end, an introducer and a guide wire, wherein said introducer comprises: a patient end nose having a patient end arranged to protrude from the patient end of said tracheostomy tube; a passage extending through said patient end nose along which said guide wire extends; and an aperture through which said guidewire protrudes at the patient end of said patient end nose, wherein the plane of said aperture extends at right angles to said passage and is inclined away from a line at right angles to said axis.

* * * * *